United States Patent [19]
Di Cesare et al.

[11] Patent Number: 5,902,722
[45] Date of Patent: May 11, 1999

[54] METHOD OF DETECTING ORGANISMS IN A SAMPLE

[75] Inventors: Joseph L. Di Cesare, Redding, Conn.; Steven M. Rosen, Mountain Lakes, N.J.

[73] Assignees: The Perkin-Elmer Corporation, Norwalk, Conn.; Roche Diagnostic Systems, Inc., Branchburg, N.J.

[21] Appl. No.: 08/985,574

[22] Filed: Dec. 5, 1997

[51] Int. Cl.$^6$ ............... C12Q 1/00; C12Q 1/68; C12Q 1/70
[52] U.S. Cl. ............... 435/4; 435/5; 435/7.31; 435/7.32; 435/7.33; 435/7.35; 435/7.36; 435/7.37; 436/518
[58] Field of Search ............... 435/5, 4, 7.2, 7.31, 435/7.32, 7.33, 7.35, 7.36, 7.37; 436/518

[56] References Cited

U.S. PATENT DOCUMENTS

| | | | |
|---|---|---|---|
| 4,514,498 | 4/1985 | Kettman et al. | 435/240 |
| 4,735,897 | 4/1988 | Vary et al. | 435/6 |
| 4,888,290 | 12/1989 | Kortright et al. | 435/240 |
| 5,019,351 | 5/1991 | Schulz . | |
| 5,527,700 | 6/1996 | Kaslow et al. | 435/240.2 |

FOREIGN PATENT DOCUMENTS 0 556 212   5/1997   European Pat. Off. .

OTHER PUBLICATIONS

Package Insert, PACE–2, Neisseria gonorrhoeae, Gen–Probe Inc, 1992.
Kato et al., Appl. Envir. Micro. 59, 3774–49 (1993).
Brindle, K.M., Biochemistry, 27 6187 (1988).

*Primary Examiner*—Donna C. Wortman
*Assistant Examiner*—Brenda G. Brumback
*Attorney, Agent, or Firm*—Ohlandt, Greeley, Ruggiero & Perle, L.L.P.; George W. Rauchfuss, Jr.

[57] ABSTRACT

The presence or absence of an organism in a sample is detected by isolating the organism from the sample by a suitable affinity matrix, releasing the organism from the affinity matrix, rupturing the cells of the organism to release total nucleic acid and hydrolyzing or digesting the total nucleic acid to form mononucleotides or individual free nucleic acid basic and inorganic phosphate to form an analyte solution, and assaying the analyte solution for the at least one presence of free nucleic acid base or inorganic phosphate to thereby determine whether the organism was present in the sample.

12 Claims, 2 Drawing Sheets

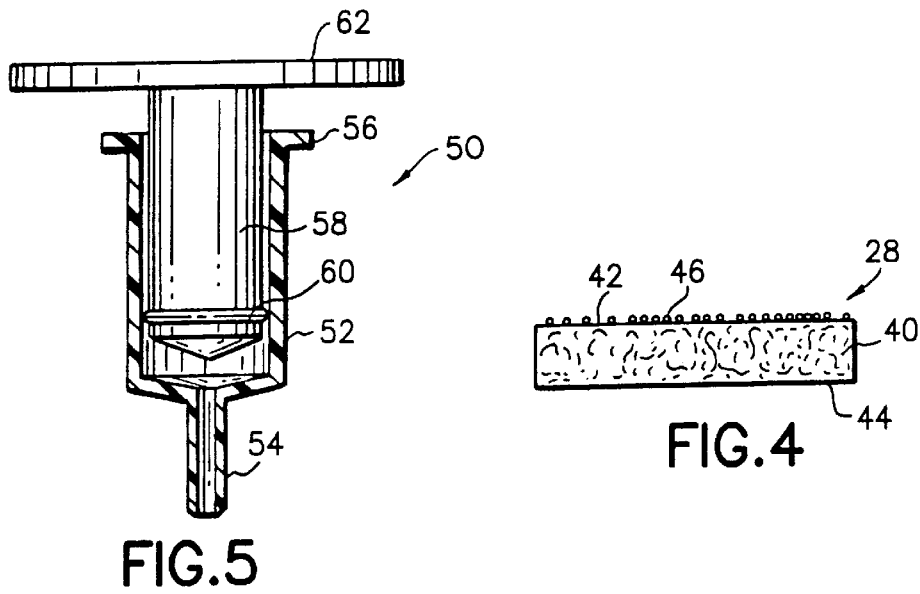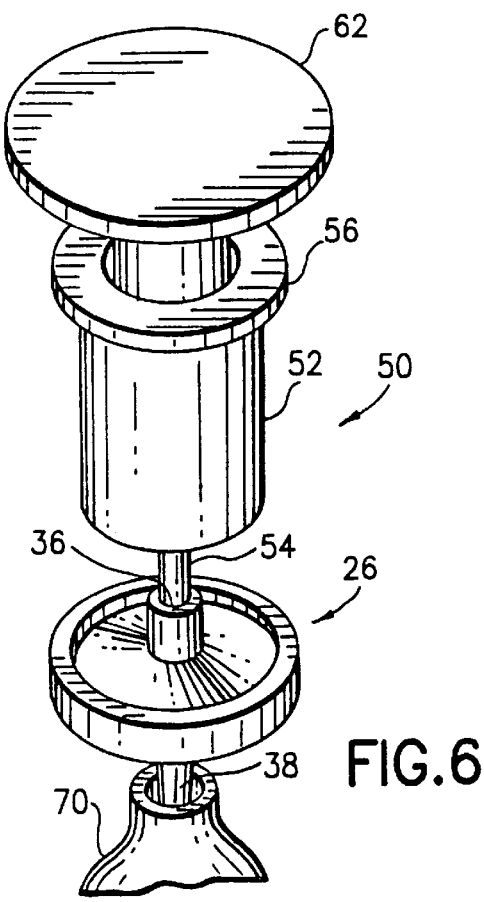

METHOD OF DETECTING ORGANISMS IN A SAMPLE

FIELD OF THE INVENTION

This invention relates to an improved method for analysis of samples for detection of or analyzing for the presence of organisms in the sample. More particularly, this invention relates to an improved method for detection or analysis of organisms, such as microorganisms and viruses, in samples permitting the detection of very low levels of organisms, even down to the presence of about a single cell thereof in a sample.

BACKGROUND OF THE INVENTION

Organisms such as microorganisms and viruses can play a significant role in the lives of plants, animals and humans for a wide variety of reasons. For example, bacterial microorganisms are involved in the spoilage of meat, wines, vegetables and dairy products and can render these foods unpalatable or even dangerous, leading to food poisoning such as that caused by Staphylococcus aureus or Clostridium botulinum. Likewise, bacteria can be of significant importance in various industries due to their fermentation capabilities. Especially significant is the fact that about 200 species of bacteria are pathogenic for humans. For example, invasive bacteria are responsible for human diseases such as several forms of pneumonia, diphtheria, leprosy, plague, dysentery, tuberculosis, cholera, lockjaw, tetanus, syphilis, gonorrhea, typhoid fever, and the like.

Similarly, viruses play a major role in infectious diseases. For example, among the many diseases caused by viruses in humans, there may be mentioned, for example, the common cold, rabies, poliomyelitis, yellow fever, encephalitis, hemorrhagic fevers, influenza and other respiratory diseases, hepatitis, warts, chicken pox, shingles, acute diarrhea, fever blisters (herpes simplex), mumps, measles, rubella, acquired immune deficiency syndrome (AIDS), certain cancers, Creutzfeldt-Jakob disease, infant gastroenteritis and the like. Viruses can also cause a wide variety of diseases in plants, such as for example, those cause by turnip yellow mosaic virus, tobacco mosaic virus, potato X virus and the like.

Likewise, fungi can be a significant source of health problem in humans or plants. For example, Madurella mycetoni fungi can produce maduromycosis or other foot infections and many fungal forms of mushrooms are known for their deadly consequences.

It is therefore clear that it is of major importance to be able to detect the presence of organism such as microorganism, for example, such as bacterium or fungi, or virus in various environments for both their desired and undesired consequences.

Over the years, a wide variety of detection techniques have been utilized for the detection of the presence of microorganism or virus in samples including incubation and the like. Polymerase chain reaction (PCR) is a recently developed significant and powerful technique for polynucleotide amplification. The technique is disclosed, for example, in U.S. Pat. Nos. 4,683,195; 4,683,202; 4,800,159 and 4,965,188. PCR may be generally described as follows. The technique is an enzymatic, in vitro synthesis method for replicating or amplifying specific target polynucleotide sequences in samples. The technique employs polymerase, deoxynucleoside triphosphates and two oligonucleotide primers that hybridize to opposite strands of the polynucleotide sample and flank the region of interest in the target polynucleotide sequence. Experimental amplification of the target sequence is obtained by a repetitive series of steps comprising template denaturation, primer annealing and extension of the annealed primers by polymerase, generally referred to as thermal cycling steps. Such a PCR technique is capable of producing amplification of the target sequence by a factor of up to about $10^9$ which can then be subject to an assay procedure appropriate for the target sequence. However, even PCR is time consuming due to the time required, about 2 hours, for the repetitive cycling steps required for amplification and replication.

It is therefore highly desirable that a method be provided for easy and rapid analysis of samples for the determination of the possible presence of organisms such as microorganisms or viruses. It is even more desirable that such a method be provided that will enable detection of even very low levels of organism, e.g. levels of 1000 or less organisms per sample, more preferably as low as about 100 or less, and even more preferably detection of as low as a single organism per sample. A further object is to provide such an assay method that can be employed without having to amplify or multiply any components of the organism and therefore can be conducted quickly and in numerous locations. Yet another object of this invention is to provide a quick and easy assay procedure that is simply to perform and not requiring complex equipment and thus suitable for on-site field use.

BRIEF DESCRIPTION OF THE DRAWINGS

The invention will be described in certain embodiments in connection with the apparatus illustrated in the drawings, in which:

FIG. 4 is an enlarged cross-sectional view of a membrane element of FIG. 3;

FIG. 5 is a partial cross-sectional view of a pressure differential providing device for use in the organism isolation step of this invention; and FIG. 6 is a partial cross-sectional view of apparatus for isolating an organism from a sample solution in the method of this invention.

SUMMARY OF THE INVENTION

Figure 1:
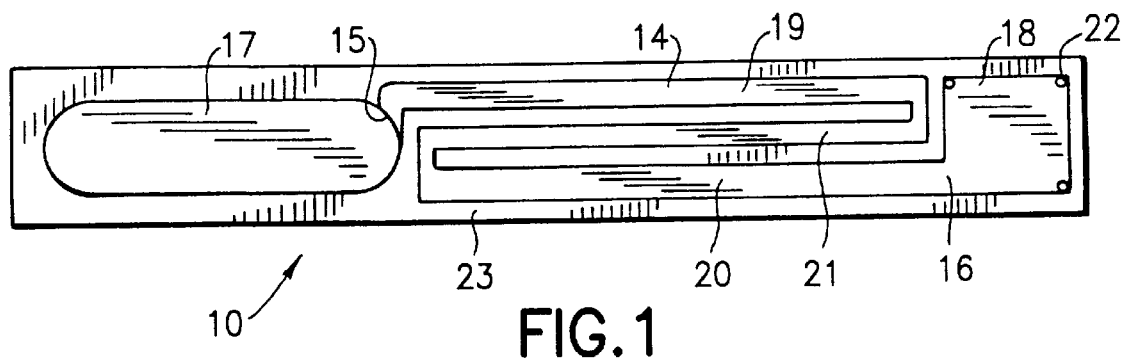
FIG. 1 is a plan view of an agglutination reaction slide assay device for agglutination reaction assays useful in the method of this invention.

The presence or absence of a target organism in a sample is detected in accordance with the method of this invention by isolating the target organism from the sample by a suitable affinity matrix, rupturing the cells of the isolated target organism to release total nucleic acid, hydrolyzing or digesting the total nucleic acid to form mononucleotides or individual free nucleic acid bases and inorganic phosphate to form an analyte solution, and assaying the analyte solution for the presence of at least one of: free nucleic acid base or inorganic phosphate to thereby determine whether the organism was present in the sample. In a preferred form of this invention, the target organism is first released from the affinity matrix before rupture of the cells and hydrolysis or digestion occurs.

The hydrolysis of the total nucleic acid of the organism into individual constituents, i.e. nucleic acid bases and inorganic phosphate, greatly increases the molecules available for assay. For example, a single E. coli bacterium contains a single molecule of dsDNA which can be hydrolyzed to approximately $15 \times 10^6$ molecules of individual nucleic acid bases and inorganic phosphate. Likewise, numerous RNA molecules within the E. coli can be hydrolyzed to approximately $100 \times 10^6$ molecules of individual nucleic acid bases and inorganic phosphate. Thereby, the single E coli bacterium provides approximately 115 million molecules for assay.

With the improved assay procedure of this invention one can detect a single bacterium per sample, or as low as 1000 to 10,000 viruses per sample.

DETAILED DESCRIPTION OF THE INVENTION

The improved assay procedure of this invention can be employed for detection of a wide variety of organism, particularly microorganisms and viruses. Microorganisms such as bacteria, fungi, yeasts and molds may be detected by the procedure of this invention. Also, viruses may be detected by the improved procedure of this invention.

Merely as exemplary of the bacteria that may be detected according to this invention, there may be mentioned *Aerobacter cloacae, Salmonella choleraesuis, Salmonella typhosa, staphylococcus aureus, Clostridium botulinum, Clostridium chauvoei, Clostridium perfringens, Clostridium tetanii, Treponema pallidum, Bungarus multicinclus, Neisseria gonorrhea, Naja naja atra, Naja nigricollis, Vibrio cholerae, Conus geographus, Conus magnus, Bordetella pertussis, Lactobacillus bifidus, Alcoligenes faecales, Fusarium sporotricloides, Anemonia sulcata, Dentroaspis angusticeps, Streptomyces Verticillus, Escherichia coli* and the like.

Merely as exemplary of the viruses that may be detected according to the assay procedure of this invention there may be mentioned polioviruses, polyomaviruses, poxviruses, coxsackieviruses, leukoviruses, parainfluenza viruses, bacterial viruses, encephalomyocarditis viruses, rhinoviruses, rotaviruses, Ebola virus, Epstein-Barr virus, arboviruses, hepatitis viruses, infectious wart viruses, herpes simplex viruses, Lassa fever virus, respiratory syncytial virus, adenoviruses, HTLV, retroviruses, papilloma viruses, turnip yellow mosaic virus, potato X virus, tobacco mosaic virus and the like.

The assay procedure of this invention can be employed to detect organisms from a wide variety of samples, such as biological samples from humans, plants or animals or environmental samples. Any suitable biological or environmental material containing or presumed to contain the organism can be employed to provide the sample. As examples of biological samples, there may be mentioned tissue or fluid isolated from an individual animal or person, including but not limited to, skin, plasma, serum, spinal fluid, lymph fluid, synovial fluid, urine, tears, blood cells, organic, tumors and in vitro cell cultures, for example. As environmental samples there may be mentioned water, effluent water, soil, sludge, wastes or sediments and the like, where an organism's presence may be suspected.

After the sample has been provided, the sample is treated to isolate the target organism from other possible organisms in the sample. The isolation is accomplished by the use of any affinity reagent or antibody for the target organism. For example, a water sample to be analyzed for the presence of an organism can be subjected to an affinity matrix such as a chromatography column or filter medium having affixed thereto an affinity reagent or antibody for the microorganism, to isolate the target organism. It will be appreciated that one skilled in the art will select the appropriate affinity reagent and matrix or antibody or hybridization probe to isolate the target organism from the sample. A suitable affinity membrane will be described hereinafter.

The isolated target organism can then be released or eluted from the affinity matrix in a known manner to provide an eluent of the cells of the organism and also to rupture the cells and release total (DNA and RNA) nucleic acid. Rupture of the cells of the organism can be accomplished in any suitable manner, such as by free-thaw cycles, by the use of a detergent such as sodium dodecyl sulfate (SDS), or with a buffered solution of SDS and the enzyme proteinase K, or by lysozyme with or without detergent or by any other suitable method, many being described in the art.

The released total nucleic acid is then hydrolyzed or digested into the individual bases and inorganic phosphate. It will be appreciated that in some instances it may be desirable to separate the released nucleic acid from the other constituents of the releasing step and this may be done according to means known in the art. For example, the released nucleic acid from the organism may be separated using a suitable nucleic acid hybridization probe for a further selective enrichment for specific organisms. The hydrolysis or digestion can be accomplished by use of a variety of hydrolytic enzymes or nucleases or phosphatases, such as endonucleases, exonucleases and alkaline phosphatases. Preferably a combination of such enzymes may be employed to facilitate and expedite the hydrolysis or digestion.

As examples of suitable nucleases, there may be mentioned Nuclease Bal 31, Exonuclease III, Exonuclease IV, Mung bean nuclease, Nuclease P1, Pancreatic deoxyribonuclease, RNase A, RNase H, RNase T1, and Nuclease S1. As example of suitable phosphatases, there may be mentioned alkaline phosphatase (*E. coli* A19), alkaline phosphatase (*E. coli* C75), calf intestinal alkaline phosphatase and shrimp alkaline phosphatase.

It will also be understood that the cell rupture operation to release total nucleic acid and the hydrolysis or digestion of the resultant total nucleic acid may, if appropriate, be combined into a single step and be conducted substantially simultaneously. Moreover, the cell rupture and hydrolysis or digestion of the resultant total nucleic acid may, if desired, be accomplished while the target organism is isolated on the affinity matrix, i.e. before or simultaneous with release of the organism from the affinity matrix.

The solution provided by the hydrolysis or digestion of the total nucleic acid of the target organism is the analyte solution to be analyzed for the presence or absence of the target organism.

Assay of the analyte solution for the presence of the nucleic acid bases or the inorganic phosphate can be accomplished in a wide variety of ways. For example, the assay may be either a semi-quantitative visual assay which can detect a level of about 1 million organisms or by a quantitative instrument assay format to detect as low as a single organism. One of the means of visual assay can be an agglutination reaction assay conducted on a suitable agglutination reaction slide assay device known in the art, such as that disclosed in the aforementioned U.S. Pat. No. 5,019,351 and illustrated in FIG. 1. The assay test element is represented by the general reference numeral 10. The test element comprises a receiving and mixing well 17 where a sample from the analyte solution to be analyzed and appropriate reagents including antibody to the target organism and particles coated with an analyte analog or conjugate are mixed. The mixture is then permitted to enter a serpentine-shaped capillary reaction track 14 through upstream capillary entrance 15. The mixture proceeds along track 14 through upstream capillary region 19, intermediate capillary region 21 and downstream capillary region 20, exiting the capillary track by downstream capillary exit 16, entering a viewing or observation region in the form of viewing well 18. Viewing region 18 can be provided with bores 22 for venting the viewing region. A wall 23 extends around receiving area 17, viewing area 18 and capillary track region 14 to provide a fluid-tight bonding around these regions. Observation of the viewing area, after traverse of the sample of analyte solution and reagents through the capillary track, will enable a result to be visually determined by the presence of or the absence of agglutination, i.e. no agglutination is a positive for the target organism and the presence of agglutination is a negative for the target organism.

While a wide variety of matrices are available for use in isolating the target organism from the sample in the initial stage of the method of this invention, it is preferred, where possible to employ a suitable porous or permeable membrane to conduct the isolation step. A suitable porous membrane and a device incorporating such a membrane are illustrated in FIGS. 2 through 6.

Figure 2:
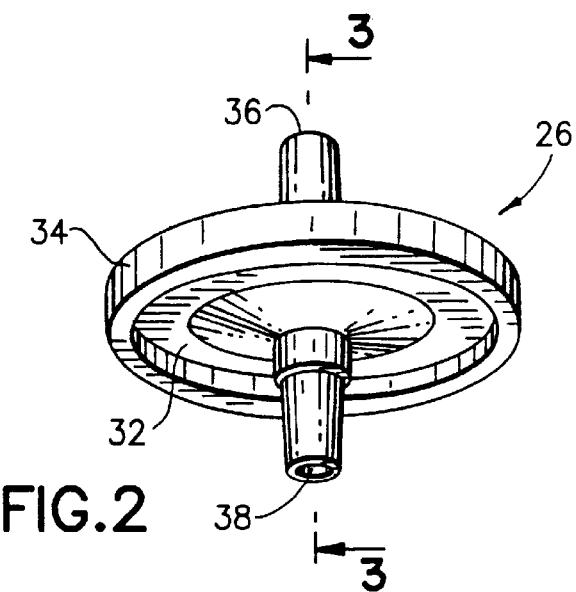
FIG. 2 is a perspective view of a permeable membrane in a fluid tight housing for use in isolating a target organism.
Figure 3:
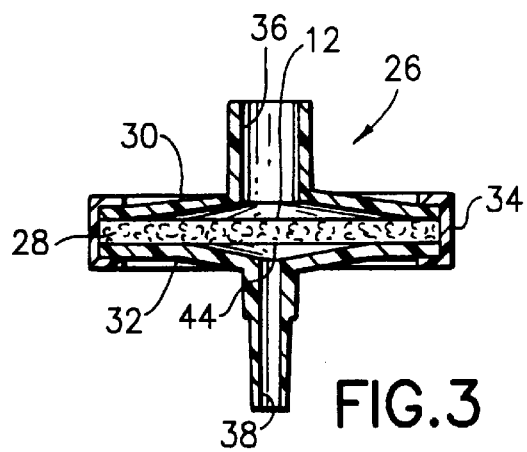
FIG. 3 is a cross-sectional view along line 3—3 of FIG. 2.

Shown in FIGS. 2, 3 and 4 is an element for such an organism isolating device, indicated generally by reference numeral 26. The element 26 comprises a suitable porous or permeable membrane 28 housed in the isolating device 26 and held between an inlet cap 30 and an outlet cap 32 by a retainer housing 34. Inlet cap 30 is provided with a generally centrally located inlet port 36 and outlet cap 32 is provided with a generally centrally located outlet port 38. Retainer housing 34 provides a fluid-tight housing around the inlet cap 30, permeable membrane 28 and outlet cap 32. The permeable membrane 28 is shown in greater detail in FIG. 4.

The membrane 28 is a disc 40 made of a permeable solid phase material which itself is inert to the organism to be isolated. The membrane disc 40 has a top surface 42 and a bottom surface 44 with holes or interstices therethrough. Particles 46, coated with an antibody or an affinity reagent to the organism, are entrapped in the pores and interstices and located on the top surface 42 of the membrane disc 40.

The pores or interstices of the membrane disc 40 will be at least slightly smaller in size or diameter than the diameter of the coated particles 46. For example, the particles may generally have a diameter of at least from about 0.6 $\mu$m or greater, and the pores or interstices will generally be in the range of from about 0.4 to about 0.7 $\mu$m, preferably from about 0.4 to 0.5 $\mu$m. Most preferably the particles may have a diameter of from about 100 to 200 $\mu$m. The disc can be composed of any suitable substance inert to the reactants, such as, for example, paper, glass fiber, cotton, cellulose, cellulose acetate and synthetic polymeric material such as polytetrafluoroethylene, polyethylene, polypropylene, polyvinylidene fluoride and the like. A preferred membrane disc will be about 25 mm in diameter and have a capacity of at least 1,000,000 organisms, most preferably a glass fiber membrane disc of said size. The particles can be made of a wide variety of suitable materials, such as, for example, silica or glass, cellulose and synthetic polymers. A preferred form of the particles is a latex of polystyrene beads.

The particles are first bound to an antibody or affinity reagent for the target organism in a generally known manner, either covalently or non-covalently. The selection of the particular material to be coated to the particles will be driven by the organism to be isolated. One will select a suitable material which has selective affinity for the organism, such as an antibody or an affinity reagent for the organism. Then, an aspiration/expulsion device, such as a manually operated syringe 50 (FIG. 5) is employed to entrap the coated particles in the pores or interstices and also to place said coated particles on the top surface of the membrane disc 40.

The syringe 50 comprises a tubular housing 52 having at one end a centrally located conduit 54 for aspiration of material into and expiration of material from the housing. At the opposite end the tubular housing terminates in a shoulder 56. Located within housing 52 is a movable tubular piston 58 held in fluid tight relationship to the interior of tubular housing 52 by a sealing means 60, such as an O-ring. External of housing 52 piston 58 is provided with a suitable handle 62 for manual aspiration and expiration of material.

Antibody or affinity reagent coated particles 46 in a suitable fluid medium are aspirated into housing 52 of syringe 50 through conduit 54, then the conduit is placed in inlet port 36 (FIG. 6) of the enrichment device 26 and the coated particles are expelled from the syringe into the enrichment device entrapping the coated particles in the pores or interstices of the disc 40 and the top surface 42 thereof with the fluid medium passing through disc 40 and out outlet port 38 into a suitable collection container 70. The syringe is then removed from inlet port 36.

The membrane disc 40 with the coated particles located in the pores and interstices thereof and on the top surface of the disc is able to bind substantially all the target organism in the sample being processed through the isolation device.

Thereafter, a sample suspected to contain the organism is aspirated into a similar syringe 50, the syringe similarly attached to inlet port 36 and the sample is expelled into isolating device 26. Target organism in the sample binds to the antibody or affinity reagent coated particles which are on the top surface of the disc 40 and entrapped in the pores and interstices of the membrane disc while the fluid in the sample permeates the disc and flows out the outlet port 38 into a suitable collection vessel or container 70.

The organism bound to the coated particles on and in the membrane disc 40 is then eluted with a small amount of elution solvent from a similar syringe 50 or squeezable container introduced into inlet pore 36 of isolation device 28 to unbind organism from the coated particles and elute the freed organism out outlet port 38 into a suitable collection vessel or container 70. The elution solvent must be one that is compatible with and does not interfere with the processing or assay steps occurring later.

After the organism from the sample has been suitably isolated and eluted in the forgoing manner, the organism is then treated in accordance with this invention to rupture the cells of the organism and release the total nucleic acid, hydrolyze or digest the total nucleic acid into free nucleic acid bases and inorganic phosphate.

After the organism has been isolated, its total nucleic acid released and the hydrolyzed into its individual free bases and inorganic phosphate, the resulting analyte solution is assayed to determine if the organism was present in the sample. The assay may be an assay of nucleic acid bases or an assay of inorganic phosphate or even an assay of both if desired. It should be mentioned that the analyte solution may need to be subjected to a cleanup step before proceeding to the assay step since the components of the hydrolysis may interfere with the assay analysis.

The individual nucleic acid bases may be assayed using various forms of immunoassay procedures employing antibody directed to the bases according to procedures well known in the art. As indicated hereinbefore a preferred form of assay is an agglutination reaction utilizing the reaction slide device of FIG. 1.

Alternatively, the assay may be an analysis based on the inorganic phosphate in the analyte solution. As examples of assays based on inorganic phosphate (Pi), there may be mentioned the assay based on converting Pi to adenosine triphosphate (ATP) and detecting the ATP, especially by a chemiluminescence procedure. As exemplary of assays based on the conversion of Pi to ATP, there may be mentioned the conversion Pi to ATP in the presence of ADP, Acetyl CoA and the enzyme acetate kinase (ACK) as reported by Kato et al., Appl. Envir. Micro. 59, 3744–49 (1993) and the conversion of Pi to ATP employing a tandem reaction, whereby a first reaction Pi, in the presence of glyceraldehyde phosphate and nicotinamide adenine dinucleotide and the enzyme glyceraldehyde phosphate dehydrogenase, is converted to 1,3-diphosphoglycerate, reduced nicotinamide, adenine dinucleotide and hydrogen and in a second reaction 1,3-diphosphoglycerate and ADP are converted to 3-phosphoglycerate and ATP as reported by Brindle, K. M., Biochemistry, 27 6187 (1988). A preferred assay for the conversion of Pi to ATP is a quantitative bioluminescence determination of ATP as it is consumed and light is emitted when luciferase (firefly, bacterial or other origin) catalyzes the oxidation of D-luciferin, such as by employing the ATP Bioluminescent Assay Kit of Sigma Chemical Co. and by use of a luminometer. The amount of light generated is proportioned to the amount of ATP present and thus the amount of Pi present from the organism.

The invention is illustrated, but not limited, by the following example of detection of gonococcal bacteria in a solution.

EXAMPLE

Monoclonal antibodies that cross-react with the alpha, beta, gamma and delta pili of gonococci are purified on a protein A column and then conjugated to 0.8 um latex beads. The antibodies are enriched by ammonium sulfate precipitation by slowly adding an equal volume of saturated (100%) ammonium sulfate to the antiserum in an ice bath to precipitate the antibodies. The precipitated antibodies are resuspended in a phosphate buffer solution (PBS) at about pH 7.0+ or −0.1 and centrifuged to provide a concentration of antibodies of about 17 mg/ml.

Commercially available white polystyrene latex microparticles of 0.8 um in a 30% stock solution are washed four times with 50 mM methyl ethane sulfonic acid (MES) buffer solution at pH 6.0+ or −0.1 at about 4 degrees C to remove the storage buffer.

The purified antibody is diluted with 50 mM MES buffer and equal volume of serial diluted antibody solution is mixed with the washed latex microparticles and stirred overnight to sensitize the latex particles. Unbound sites on the latex particles are blocked by adding an equal volume of 100 mg/ml Bovine Serum Albumin (BSA) in MES buffer to the antibody-latex microparticle mix. After an hour of blocking, the latex-antibody-BSA-Mixture is washed and resuspended in 50 mM MES buffer and the final latex solution is adjusted to 10% solids.

Employing a syringe, 0.6 ml of the 100% solid latex particles-antibody-BSA-Mixture is aspirated into the syringe and expelled therefrom at a flow rate of 0.5 ml/min. through a glass fiber membrane disk, having 0.45 um pores or interstices in an enrichment device as illustrated in FIG. 6 to trap the bound latex particles in the pores and interstices and on the top surface of the membrane disk. Thereafter, using a syringe 50 ml of sample solution of bacteria known to contain >10 gonococci per ml are passed through the disk at a rate of 3–10 ml/minute to bind the bacteria in the sample.

After the bacteria are bound to the membrane, the membrane is washed with 50 ml of PBS buffer to remove any non-specifically bound microorganisms.

The gonococci bacteria are removed from the membrane using a lysing buffer containing 50 mM glucose, 0.2 M NaOH and 0.2% sodium dodecyl sulfate. One ml of the lysing buffer is passed through the membrane using a syringe and collected. The membrane is incubated on ice for 5 minutes and another 1 ml aliquot of the lysing buffer is passed through the membrane and collected. 1.5 ml of a solution containing 60 ml of 5.0 M Potassium Acetate, 11.5 ml of glacial acetic acid and 28.5 ml of water is added to the 2 ml of the collected eluent and incubated on ice for an additional 5 minutes. An equal volume (3.5 ml) of phenol/chloroform is added and mixed by vortexing and transfer of supernatant to a fresh tube. The DNA is precipitated with 2 volumes of ethanol at room temperature. The DNA sample is centrifuged at 12,000 RPM for 10 minutes and the supernatant aspirated. The DNA pellet is dried and then rinsed in 70% ethanol. The nucleic acids are dissolved in 50 ul of TE buffer (10 mM tri(hydroxymethyl)aminomethane and 1 mM EDTA).

All of the DNA is digested with 10 units each of EcoRI and BamHi restriction enzymes and Bal 31 nuclease to generate mononucleotide bases and inorganic phosphate. The digestion takes place at 37° C. and for 1 hour. This is the analyte solution.

Assay of individual nucleosides in the analyte solution from the hydrolysis of the DNA and RNA in the sample can be conducted numerous ways. The following describes two exemplary ways, namely by slide agglutination reaction and by ELISA assay.

Assay of the isolated nucleic acids is conducted by placing 11 ul of the sample analyte solution, about 50 ul of nucleotide-BSA coated latex microparticles, about 50 ul of antibody to the nucleotides and 50 ul of reaction buffer in the receiving and mixing well of an agglutination slide apparatus, as illustrated in FIG. 1. The components are mixed with a spatula and allowed to flow down the capillary to the viewing area of the slide. The absence of agglutinated latex particles in the viewing area confirms the presence of the nucleotides and indirectly, the specific gonococci bacterium. In contradistinction, if the sample does not contain nucleic acids then the viewing area will appear agglutinated.

For the ELISA assay procedure, five individual nucleotides are covalently conjugated via a linker to the carrier protein bovine thyroglobulin (BTG) in a ratio of 1:75 (BTG:nucleotide). The conjugations are performed as individual reactions. The conjugated carrier protein is dialyzed extensively against PBS in order to remove the unconjugated nucleotides and produce the desired immunogens. The conjugates are mixed together in an equimolar ratio, so that each animal immunized will produce antibodies to all five nucleotide bases. Six months to one year old goats, sheep and rabbits are immunized with 3 mg of these immunogens emulsified in complete Freund's adjuvant. Subsequent immunizations are performed using incomplete Freund's adjuvant. The anti-nucleotide antibody thus generated evaluated by ELISA assay for binding to a BSA-nucleotide coated plate and for the ability of the binding to be inhibited by soluble nucleotides.

Ninety-six well microliter plates are coated with 50 ul of 5 ug/mL Nucleotide(s)-Bovine Serum Albumin (BSA) conjugate diluted in PBS and incubated for 2 hours at room temperature. The liquid is removed from the plates by flicking them into the sink and by blotting the plates onto absorbent paper. One hundred microliters of 1% BSA in PBS/azide was dispensed into each well and the plates are incubated for 1 hour at room temperature. Following the incubation, the plates are washed three times with PBS/0.01% Tween 20. 25 ul of anti-nucleotide antibody are added to each well in the presence or absence of free nucleotide as inhibitor. The plates are covered and incubated at 37° C. for 1 hour. The plates are washed on a plate washer three times and 50 uL of anti-mouse antibody conjugated to alkaline phosphatase are added to each well. The plates are incubated at 37° C. for 1 hour and are then washed as described above. The assay is developed by the addition of 1 mg/mL para-nitrophenol phosphate dissolved in diethanolamine buffer at pH 9.8. The substrate containing plates are incubated at room temperature for 30 minutes. Fifty uL of 3 M NaOH are added to the wells to stop the enzyme reaction. The plates were read immediately at 405 nm.

A standard curve for displacement is generated by the addition of an equimolar mixture of 5 nucleotides guanine, adenine, thymine, cytosine and uracil. The nucleotide content of the analyte solution is then evaluated based upon comparison with the standard curve values.

Assay of isolated inorganic phosphate in the analyte solution is conducted by use of an adenosine-5'-triphosphate (ATP) bioluminescence assay kit, such as Sigma Chemical Co.'s Assay Kit, Stock No. FL-AA. Isolated inorganic phosphate (Pi) in the analyte solution is first converted to ATP. The inorganic phosphate can be converted to ATP in the presence of the enzyme acetate kinase, Coenzyme A and adenosine diphosphate according to procedures known to those skilled in the art. After conversion of Pi to ATP, the assay is begun by adding 0.1 ml of the ATP assay mix from the assay kit to a reaction vial, swirling it and letting it stand for about 3 minutes at room temperature to hydrolyze any androgenous ATP thereby decreasing background. Then 0.1 ml of analyte solution is rapidly added to the reaction vial, swirled briskly and the amount of light produced is immediately measured with a luminometer compared to background light produced by a 0.1 ml sample diluent to determine the amount of light proportional to the amount of ATP or inorganic phosphate in the analyte solution. The amount of light produced by the inorganic phosphate in the analyte solution is an indication of the presence of the gonococci bacterium in the sample.

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A method for detecting the presence of a target organism in a sample, said method comprising:

(1) providing a sample which may contain the target organism;

(2) isolating the target organism from the sample by a matrix having attached thereto an affinity reagent for the target organism;

(3) treating the isolated target organism to rupture cells of the organism and release total nucleic acid;

(4) hydrolyzing or digesting the total nucleic acid of the organism into individual free nucleic acid bases and inorganic phosphate to form an analyte solution; and (5) assaying the analyte solution for the presence of at least one of (a) free nucleic acid base or (b) inorganic phosphate to determine whether the organism was present in the sample.

2. A method according to claim 1 comprising releasing the isolated target organism from the affinity matrix prior to treating the isolated target organism to rupture the cells of the organism and release total nucleic acid.

3. A method according to claim 2 wherein the assaying step (5) comprises assaying for presence of free nucleic acid base employing an antibody for the base.

4. A method according to claim 2 wherein the assaying step (5) comprises assaying for presence of inorganic phosphate by converting inorganic phosphate of the analyte solution into adenosine triphosphate and detecting the presence of adenosine triphosphate.

5. A method according to claim 4 wherein the presence of adenosine triphosphate is detected in a luciferase assay in which adenosine triphosphate is consumed and light is emitted when luciferase enzyme catalyzes the oxidation of D-luciferin.

6. A method according to claim 5 wherein the amount of adenosine triphosphate is determined by the amount of light generated in the luciferase assay.

7. A method according to claim 2 wherein assaying step (5) comprises a chemiluminescence step.

8. A method according to claim 2 wherein the organism is a bacterium, a fungus or a virus.

9. A method according to claim 8 wherein the organism is a bacterium selected from the group consisting of Escherichia, Neisseria, Salmonella, Staphylococcus, Clostridium, Treponema, Chlamydia, Haemophilus, Vibrio, Bordetella, Lactobacillus, Shigella, Streptomyces and Pasteurella bacteria.

10. A method according to claim 2 wherein the assaying step (5) comprises an agglutination reaction assay conducted on a reaction slide.

11. A method according to claim 2 wherein isolating step (2) comprises contacting the sample with a membrane having pores or interstices therein and having latex particles coated with an affinity reagent to the organism located on a surface and in the pores and interstices of the membrane.

12. A method according to claim 11 wherein the affinity reagent is an antibody to the organism.

* * * * *